United States Patent
Clifton

(10) Patent No.: US 11,547,293 B2
(45) Date of Patent: Jan. 10, 2023

(54) RETINAL POSITION TRACKING

(71) Applicant: Optos PLC, Dunfermline Fife (GB)

(72) Inventor: David Clifton, Dunfermline (GB)

(73) Assignee: OPTOS PLC, Dunfermline (GB)

( * ) Notice: Subject to any disclaimer, the term of this patent is extended or adjusted under 35 U.S.C. 154(b) by 314 days.

(21) Appl. No.: 16/637,052

(22) PCT Filed: Aug. 14, 2017

(86) PCT No.: PCT/EP2017/070580
§ 371 (c)(1),
(2) Date: Feb. 6, 2020

(87) PCT Pub. No.: WO2019/034231
PCT Pub. Date: Feb. 21, 2019

(65) Prior Publication Data
US 2020/0237209 A1 Jul. 30, 2020

(51) Int. Cl.
*A61B 3/00* (2006.01)
*G06T 7/246* (2017.01)
(Continued)

(52) U.S. Cl.
CPC .............. *A61B 3/0025* (2013.01); *A61B 3/102* (2013.01); *A61B 3/12* (2013.01); *G06T 7/248* (2017.01);
(Continued)

(58) Field of Classification Search
CPC ......... A61B 3/0025; A61B 3/102; A61B 3/12; G06T 7/248; G06T 2207/10016; G06T 2207/10101; G06T 2207/30041
See application file for complete search history.

(56) References Cited

U.S. PATENT DOCUMENTS

| | | |
|---|---|---|
| 5,196,929 A | 3/1993 | Miyasaka |
| 5,815,242 A | 9/1998 | Anderson et al. |

(Continued)

FOREIGN PATENT DOCUMENTS

| | | | |
|---|---|---|---|
| CN | 103339929 | * 10/2013 | ............ G06T 7/001 |
| CN | 103339929 A | 10/2013 | |

(Continued)

OTHER PUBLICATIONS

Zainab et al, ("Retinal Image Analysis for Diagnosis of Macular Edema using Digital Fundus Images", IEEE 2013) (Year: 2013).*
(Continued)

*Primary Examiner* — Amara Abdi
(74) *Attorney, Agent, or Firm* — DeLucia, Mlynar & Associates LLP

(57) ABSTRACT

A method of processing a sequence of images of a retina acquired by an ophthalmic device to generate retinal position tracking information indicative of retina movement during acquisition. The method includes (i) receiving one or more images of the retina; (ii) calculating a cross-correlation between a reference image and an image based on the received image(s) to acquire an offset between the image and reference image; and repeating processes (i) and (ii) to acquire, as the tracking information, respective offsets for images that are based on the respective received image(s). Another step includes modifying the reference image during the repeating, by determining a measure of similarity between correspondingly located regions of pixels in two or more received images and accentuating features in the reference image representing structures of the imaged retina in relation to other features in the reference image based on the determined measure of similarity.

21 Claims, 11 Drawing Sheets

(51) Int. Cl.
*A61B 3/10* (2006.01)
*A61B 3/12* (2006.01)
(52) U.S. Cl.
CPC ............ *G06T 2207/10016* (2013.01); *G06T 2207/10101* (2013.01); *G06T 2207/30041* (2013.01)

(56) References Cited

U.S. PATENT DOCUMENTS

| | | | |
|---|---|---|---|
| 5,832,110 A | 11/1998 | Hull | |
| 6,042,232 A | 3/2000 | Luce et al. | |
| 6,095,989 A | 8/2000 | Hay et al. | |
| 9,454,817 B2 | 9/2016 | Clifton et al. | |
| 9,482,868 B2 | 11/2016 | Sasaki et al. | |
| 9,795,294 B1* | 10/2017 | Nozato | A61B 3/0025 |
| 10,362,933 B2* | 7/2019 | Goto | A61B 3/102 |
| 2001/0022859 A1 | 9/2001 | Okabayashi et al. | |
| 2004/0105074 A1* | 6/2004 | Soliz | G06T 7/593 |
| | | | 351/206 |
| 2005/0119642 A1 | 6/2005 | Grcu et al. | |
| 2006/0011928 A1 | 1/2006 | Sorg et al. | |
| 2006/0002632 A1 | 5/2006 | Fu et al. | |
| 2006/0228011 A1* | 10/2006 | Everett | A61B 3/102 |
| | | | 382/128 |
| 2008/0204891 A1 | 8/2008 | Tallaron et al. | |
| 2010/0141895 A1 | 6/2010 | Cairns et al. | |
| 2010/0149489 A1 | 6/2010 | Kikawa et al. | |
| 2011/0080558 A1 | 4/2011 | Marhall et al. | |
| 2011/0188726 A1* | 8/2011 | Nathaniel | A61B 6/4441 |
| | | | 378/42 |
| 2012/0154747 A1 | 6/2012 | Makihira | |
| 2012/0229763 A1 | 9/2012 | Suehira et al. | |
| 2012/0327365 A1 | 12/2012 | Makihira | |
| 2013/0010259 A1 | 1/2013 | Carnevale | |
| 2013/0016320 A1 | 1/2013 | Naba | |
| 2013/0070988 A1 | 3/2013 | Makihira | |
| 2013/0182219 A1 | 7/2013 | Numajiri et al. | |
| 2013/0215386 A1 | 8/2013 | Utagawa et al. | |
| 2013/0235342 A1 | 9/2013 | Makihira | |
| 2014/0063460 A1* | 3/2014 | Borycki | G06T 7/337 |
| | | | 351/208 |
| 2014/0226130 A1* | 8/2014 | Everett | A61B 3/102 |
| | | | 351/210 |
| 2014/0300864 A1* | 10/2014 | Fukuma | A61B 3/102 |
| | | | 351/206 |
| 2014/0334707 A1 | 11/2014 | Teiwes et al. | |
| 2015/0016051 A1 | 1/2015 | Herring et al. | |
| 2015/0138502 A1 | 5/2015 | Moriguchi et al. | |
| 2015/0216408 A1 | 8/2015 | Brown et al. | |
| 2016/0066888 A1 | 3/2016 | Yao et al. | |
| 2016/0183780 A1 | 6/2016 | Docherty | |
| 2017/0206657 A1* | 7/2017 | Nozato | G06T 7/20 |
| 2020/0275834 A1* | 9/2020 | Tokuda | A61B 3/0041 |

FOREIGN PATENT DOCUMENTS

| | | | |
|---|---|---|---|
| DE | 11 2013 004379 T5 | 5/2015 | |
| EP | 2 702 930 A1 | 3/2014 | |
| EP | 2702930 A1 * | 3/2014 | A61B 3/102 |
| JP | 3490088 B2 | 9/1997 | |
| JP | 2004-214733 A | 7/2004 | |
| JP | 2008 289579 A | 12/2008 | |
| JP | 5330236 B2 | 12/2009 | |
| JP | 2014171755 A | 9/2014 | |
| JP | 2015198893 A | 11/2015 | |
| JP | 2015204609 A | 11/2015 | |
| WO | WO2006/103281 A1 | 10/2006 | |
| WO | 2012072995 A1 | 7/2012 | |
| WO | 2014053824 A1 | 4/2014 | |
| WO | WO2014/053824 A1 | 4/2014 | |

OTHER PUBLICATIONS

Shantala et al, (Abnormality Detection in retinal images using Haar wavelet and First order features, IEEE 2016) (Year: 2016).*
International Search Report dated May 22, 2018 in international application No. PCT/EP2017/070580.
Written opinion of the International Searching Authority issued in international application No. PCT/EP2017/070580.
U.S. Appl. No. 16/636,999, filed Feb. 6, 2020.
U.S. Appl. No. 16/637,023, filed Feb. 6, 2020.
U.S. Appl. No. 16/637,075, filed Feb. 6, 2020.
Yu Kato et al., Noise Reduction for Tomographic Images Based on Locally Weighted Averaging (A method for removing noise in medical Tomographic Images using a local on Weighted Average), FIT 2015 14th Information Science Technology Forum, 3-part collection of papers, reviewed paper/general research papers, Image Recognition/Media Comporehension, Graphics/Image, Human-Communication & Interaction, Education/Engineering/Multimedia Applications, 2015; pp. 243-244.
Notice of Reasons for Rejection dated Jun. 15, 2021 in Japanese Application No. 2020-508479 (2 sheets); English translation attached (3 sheets).
Office Action dated Dec. 31, 2021, in Chinese Patent Application No. 2017800954399 (7 sheets); Summary of the Objections in the Office Action attached (1 sheet).

* cited by examiner

RETINAL POSITION TRACKING

This application is a national phase filing under 37 U.S.C. § 371 based on International Application No. PCT/EP2017/070580, filed Aug. 14, 2017, and claims the benefit of priority of that International Application. The contents of the International Application are incorporated by reference herein.

TECHNICAL FIELD

The present invention generally relates to the field of image processing and, more particularly, to the processing of images of a retina acquired by an ophthalmic device having an imaging section to generate retinal position tracking information that is indicative of a movement of the retina during the image acquisition.

BACKGROUND

Ophthalmic devices having an imaging section such as a scanning laser ophthalmoscope (SLO), which can use the imaging section to generate a stream of retinal images for tracking eye movements, are often used in optical coherence tomography (OCT) and other kinds of ophthalmic work. The imaging section typically acquires the images at high frame rates and under relatively low levels of infrared (IR) illumination. The acquired images therefore tend to be of low dynamic range and exhibit poor signal-to-noise. In addition, small eye movements can affect the image lighting in such a way that retinal feature variation and fragmentation can occur from one image frame to another. These factors can make it difficult to achieve satisfactory positional confidence, repeatability, accuracy and stability during eye movement tracking or in post-processing of the images.

SUMMARY

The inventors have devised a method of processing a sequence of images of a retina acquired by an ophthalmic device having an imaging section to generate retinal position tracking information that is indicative of a movement of the retina during the acquisition of the sequence of images. The method comprises: (i) receiving one or more images of the retina; (ii) calculating a cross-correlation between a reference image and an image based on one or more of the received images to acquire an offset between the image and the reference image; and repeating processes (i) and (ii) to acquire, as the retinal position tracking information, respective offsets for the images that are based on the respective one or more received images. The method further comprises modifying the reference image while processes (i) and (ii) are being repeated, by determining a measure of similarity between correspondingly located regions of pixels in two or more of the received images and accentuating features in the reference image representing structures of the imaged retina in relation to other features in the reference image based on the determined measure of similarity.

The inventors have further devised a non-transitory computer-readable storage medium and a signal carrying computer program instructions which, when executed by a processor, cause the processor to perform the method set out above.

The inventors have further devised an image processing apparatus configured to process a sequence of images of a retina acquired by an ophthalmic device to generate retinal position tracking information indicative of a movement of the retina during the acquisition of the sequence of images, the image processing apparatus comprising a processor and a memory storing computer program instructions which, when executed by the processor, cause the processor to perform the method set out above.

The inventors have further devised an ophthalmic device comprising an optical coherence tomography, OCT, imaging module configured to acquire OCT images of a retina of an eye by scanning a beam of light across the retina and processing a reflection of the beam from the retina, and a tracking image acquisition module configured to acquire a sequence of images of the retina for tracking a movement of the retina while the OCT imaging module acquires the OCT images. The ophthalmic device further comprises a controller comprising the image processing apparatus set out above that is configured to process the sequence of images to generate retinal position tracking information indicative of the movement of the retina during the acquisition of the OCT images. The controller is configured to control the OCT imaging module using the retinal position tracking information so as to at stabilise the beam during the acquisition of the OCT images.

BRIEF DESCRIPTION OF THE DRAWINGS

Embodiments of the invention will now be explained in detail, by way of example only, with reference to the accompanying figures, in which.

DETAILED DESCRIPTION OF EMBODIMENTS

Figure 1:
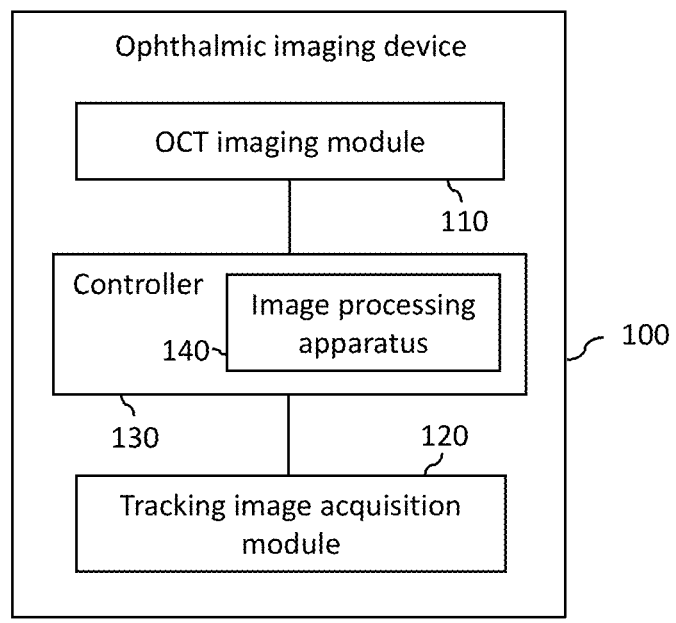
FIG. 1 is a schematic illustration of an ophthalmic device according to an embodiment of the present invention.

FIG. 1 is a schematic illustration of an ophthalmic device 100 according to an embodiment of the present invention.

The ophthalmic device 100 comprises an optical coherence tomography (OCT) imaging module 110 operable to acquire OCT images of a retina of an eye by scanning across the retina an OCT sample beam generated by a super luminescent diode (SLD) or other light source, which may operate in any part of the near-infrared or infrared spectrum, and processing a reflection of the sample beam from the retina. The ophthalmic device 100 also includes a tracking image acquisition module 120 configured to acquire image data in any suitable format that represents a sequence of images of the retina for tracking a movement of the retina while the OCT imaging module 110 acquires the OCT images. The tracking image acquisition module 120 may, as in the present embodiment, comprise a scanning laser ophthalmoscope (SLO). The tracking image acquisition module 120 may be configured to acquire the tracking images (as infrared (IR) SLO images, for example) at a high frame rate, typically 50 to 100 Hz. The acquired images may thus form, in effect, a real-time movie of the scanned region of the retina.

The ophthalmic device 100 also has a controller 130 comprising an image processing apparatus 140, which is configured to process the sequence of images to generate retinal position tracking information that is indicative of the movement of the retina during the acquisition of the OCT images as described in more detail below. An advantage of the image processing algorithm of the embodiment is its ability to acquire reliable retinal position tracking information even from low illumination, low resolution and poor signal-to-noise images that are typically acquired when IR illumination is used for the comfort of the patient and to avoid distracting the patient from maintaining a fixed gaze. An additional advantage of the algorithm in at least some embodiments is its potential to accentuate valid features for tracking in relation to features that are not valid for tracking, which may not move in correspondence with the retinal position, such as reflex and lid and lash etc. (tracking to these invalid features would not provide accurate, consistent information on how the retina is moving and could bias the tracking algorithm away from the true retinal motion). The algorithm involves using inter-image frame information, automatically identified as been common and consistent, but not necessarily at the same position, across multiple image frames, being accentuated in the reference image whilst at the same time attenuating information in the reference image that is not common. The noise- and artefact-tolerant nature of the algorithm is particularly important since design constraints (for example, the need to use IR illumination and laser power constraints) for fast frame rate SLO images tend to mean the tracking data will generally be of relatively low quality and poor signal-to-noise relative to a diagnostic SLO image. An additional problem is that small eye movements can affect the image lighting in such a way that feature variation from frame to frame can make it difficult to acquire reliable retinal position tracking information. As will be described in more detail below, the image processing method of an embodiment involves using frame-to-frame information, automatically identified as been common and valid across more than one frame, being accentuated in a reference frame relative to information that is not common to the frames.

The controller 130 is configured to control the OCT imaging module 110 using the retinal position tracking information generated by the image processing apparatus 140 so as to stabilise the OCT sample beam (in other words, at least partially compensate for movements of the retina as indicated by the retinal position tracking information) during the acquisition of the OCT images, and therefore improve sharpness and detail in the OCT images. By way of a non-limiting example, a combined SLO-OCT imaging system comprising such an OCT imaging module and tracking image acquisition module is described in more detail in International Patent Application No. PCT/BG2013/052556 (published as WO2014/053824 A1), the contents of which are incorporated herein by reference in their entirety.

It should be noted, however, that the retinal position tracking information acquired by the image processing apparatus 140 need not be used for control of the OCT imaging module 110 or other kind of imaging device or part thereof to compensate for eye movements, and may instead be used in post-processing of the acquired sequence of images, for example. It should be noted that the retinal position tracking information may be used not only in ophthalmic imaging devices but also in other kinds of ophthalmic device (such as those used in laser eye surgery and other types of ophthalmic intervention) to compensate for and/or track eye movements.

Figure 2:
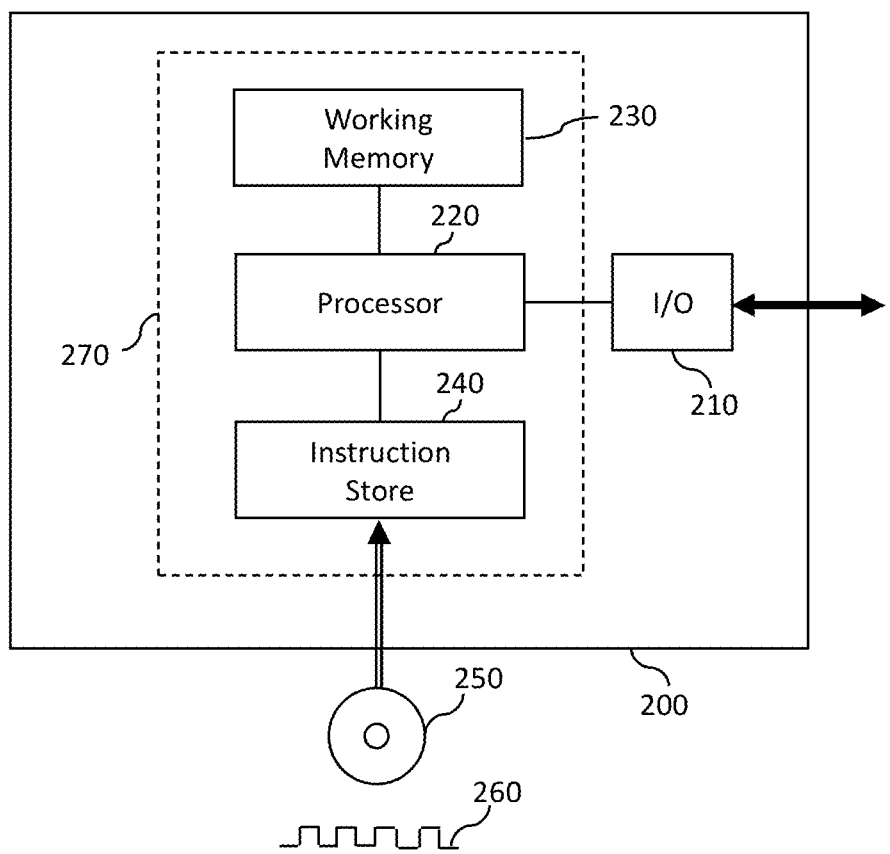
FIG. 2 is a schematic illustration of an implementation of the image processing apparatus of the controller of the ophthalmic device in programmable signal processing hardware.

FIG. 2 is a schematic illustration of an exemplary implementation of the image processing apparatus 140 in programmable signal processing hardware. The controller 130 of the ophthalmic device 100 may be implemented in the same way.

The signal processing apparatus 200 shown in FIG. 2 comprises an input/output (I/O) section 210 for receiving the images from the tracking image acquisition module 120. The signal processing apparatus 200 further comprises a processor 220, a working memory 230 (e.g. a random access memory) and an instruction store 240 storing computer-readable instructions which, when executed by the processor 220, cause the processor 220 to perform the processing operations hereinafter described to process a sequence of the acquired retinal images to generate the retinal position tracking information. The instruction store 240 may comprise a ROM (e.g. in the form of an electrically-erasable programmable read-only memory (EEPROM) or flash memory) which is pre-loaded with the computer-readable instructions. Alternatively, the instruction store 240 may comprise a RAM or similar type of memory, and the computer-readable instructions can be input thereto from a computer program product, such as a computer-readable storage medium 250 such as a CD-ROM, etc. or a computer-readable signal 260 carrying the computer-readable instructions.

Figure 3:
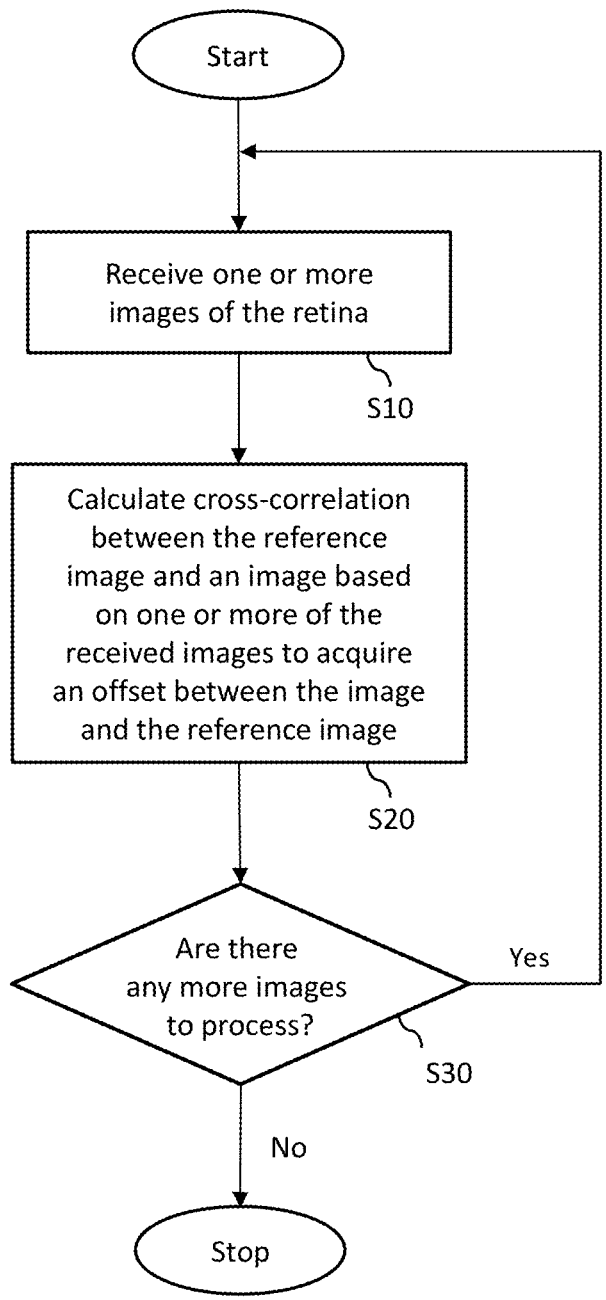
FIG. 3 is a flow diagram illustrating a process by which a sequence of images of a retina acquired by the ophthalmic device is processed by the image processing apparatus to generate retinal position tracking information in a first embodiment of the present invention.

FIG. 3 is a flow chart illustrating a process by which the image processing apparatus 140 processes a sequence of images of a retina acquired by an ophthalmic device 100 to generate the retinal position tracking information.

In process S10, the image processing apparatus 140 receives one or more images of the retina. The image processing apparatus 140 may, as in the present embodiment, receive a single image of the retina in process S10, or may alternatively receive two or more images of the retina in process S10.

In process S20, the image processing apparatus 140 calculates a cross-correlation between the received image and a reference image to acquire an offset between the received image and the reference image, using any well-known cross-correlation algorithm. The offset between the received image and the reference image may be acquired only when the calculated cross-correlation fulfils a predetermined condition (e.g. when the value of the cross-correlation peak exceeds a threshold). The acquired offset may, as in the present embodiment, comprise a translational offset ($\Delta x$ in an x-direction, and $\Delta y$ in a y-direction), as well as a rotational (angular) offset ($\Delta \theta$), between the received image and the reference image. The offset thus defines a transformation for mapping one image onto the other, so that, e.g. vasculature and/or other features of the imaged retina would overlap in a superposition of the two images. The degree of translation $\Delta x$, $\Delta y$ can be determined from the location of a peak in the calculated cross-correlation surface, and the angular offset $\Delta \theta$ can be computed from a rotation of the second image at fixed increments from a zero rotation and determining which increment provides the highest cross-correlation peak.

Although the acquired offset comprises both a translational offset and a rotational offset between the received image and the reference image in the present embodiment, in other embodiments, the acquired offset may be either a translational offset (in one or both of the x-direction and the y-direction), or a rotational offset, between the received image and the reference image, depending on the type(s) of relative movement of the retina and the ophthalmic device that are anticipated to occur during imaging.

In process S20, the image processing apparatus may more generally calculate a cross-correlation between the reference image and an image that is based on one or more of the received images (in other words, a cross-correlation between the reference image and an image of the received images (as described above), or a cross-correlation between the reference image and an image that is derived from the one or more received images), to acquire an offset between said image and the reference image. For example, the image that is cross-correlated with the reference image may be obtained by averaging two or more of the received images (e.g. two or more consecutive received images in the sequence), or otherwise processing two or more of the received images.

In process S30, the image processing apparatus 140 determines whether there are any more retinal images to process. If there are one or more further images to process, then the process loops back to process S10, otherwise the process is terminated. Through repeated performance of processes S10 and S20, the image processing apparatus 140 acquires respective offsets for the images in the sequence as the retinal position tracking information. The process may alternatively lock (thereby locking the reference frame) in cases where the confidence value F described below has risen and then remains unchanging as frames are processed. This would be indicative that, in a particular case (where there is little change occurring), there are no more improvements to be made.

While processes S10 and S20 are being repeated, the image processing apparatus 140 modifies the reference image by determining a measure of similarity between the content of correspondingly located and identically shaped regions of pixels in two or more of the received images and, based on the determined measure of similarity, accentuating at least some features in the reference image representing structures of the imaged retina in relation to other features in the reference image. The reference image is thus adaptive to changing conditions of the images being processed, which may enable a high degree of robustness in tracking to be achieved since the signal-to-noise (or other indicator of a ratio of 'useful information' for tracking to 'non-useful information' for tracking) in the reference image improves and the adverse effect of variable lighting between images can be reduced. As will be explained in the following, the reference image represents an accumulation of selected information from a number of image frames, with some points in the reference image being accentuated in relation to other points, depending on the analysis of the images herein described.

By way of a non-limiting example, the process by which the image processing apparatus 140 of the present embodiment modifies the reference image will now be described with reference to FIGS. 4 to 10.

Figure 4:
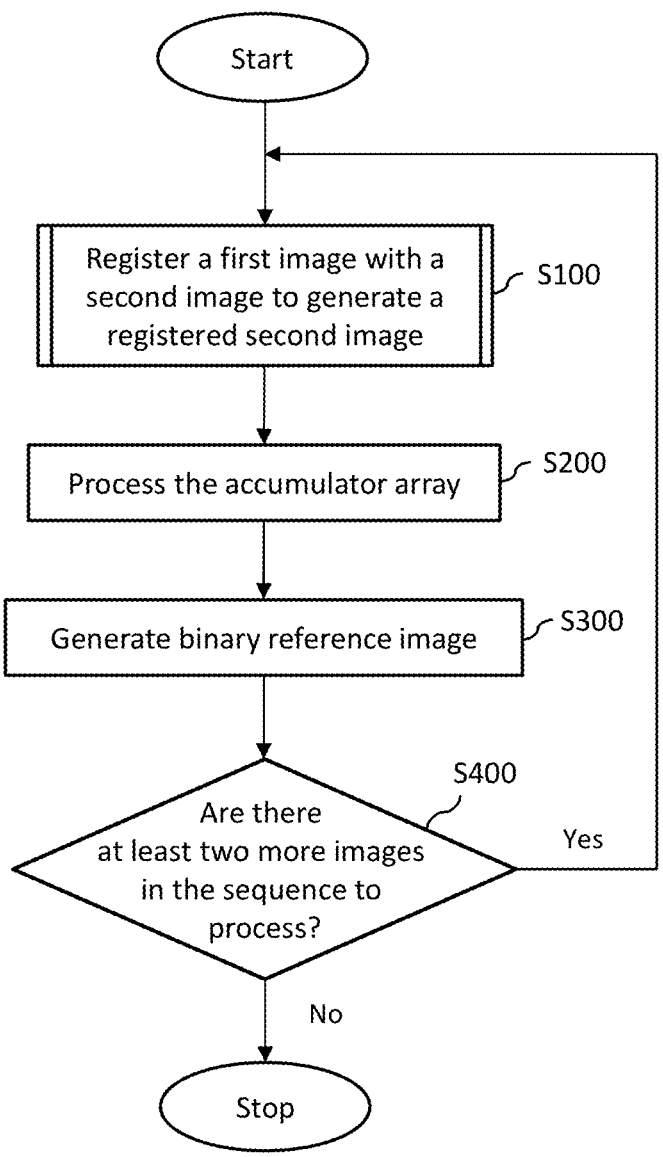
FIG. 4 is a flow diagram illustrating a process by which the reference image used in the process of FIG. 3 is modified to accentuate features therein representing structures of the imaged retina in relation to other features in the reference image.
Figure 5:
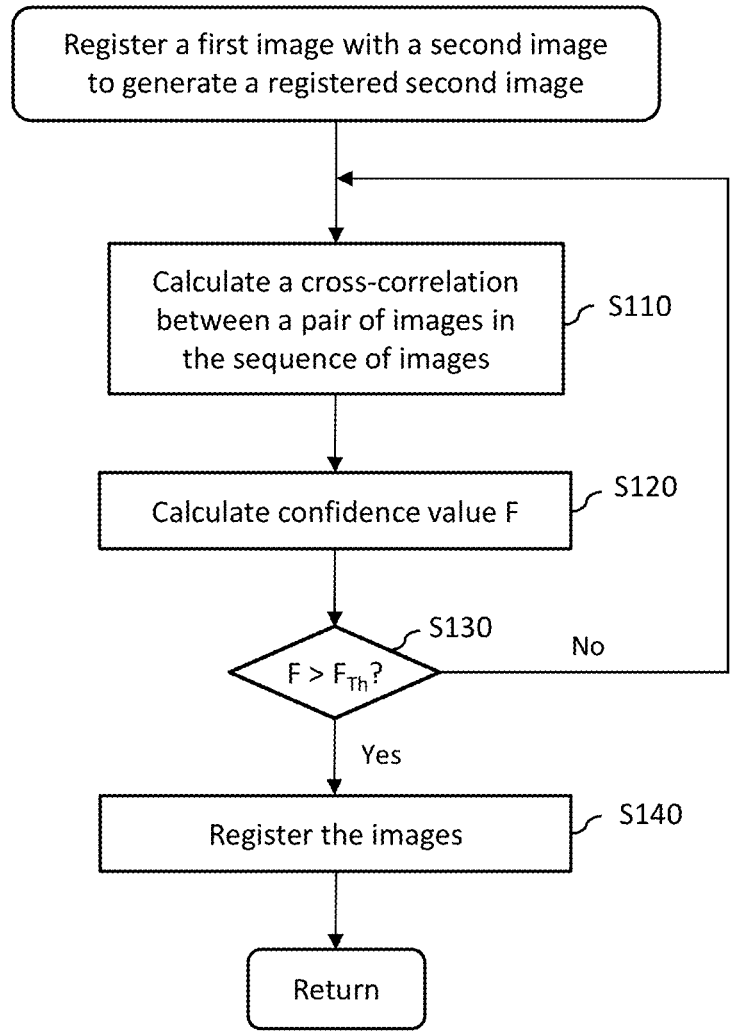
FIG. 5 is a flow diagram illustrating a process by which two received images are registered with respect to one another.
Figure 7:
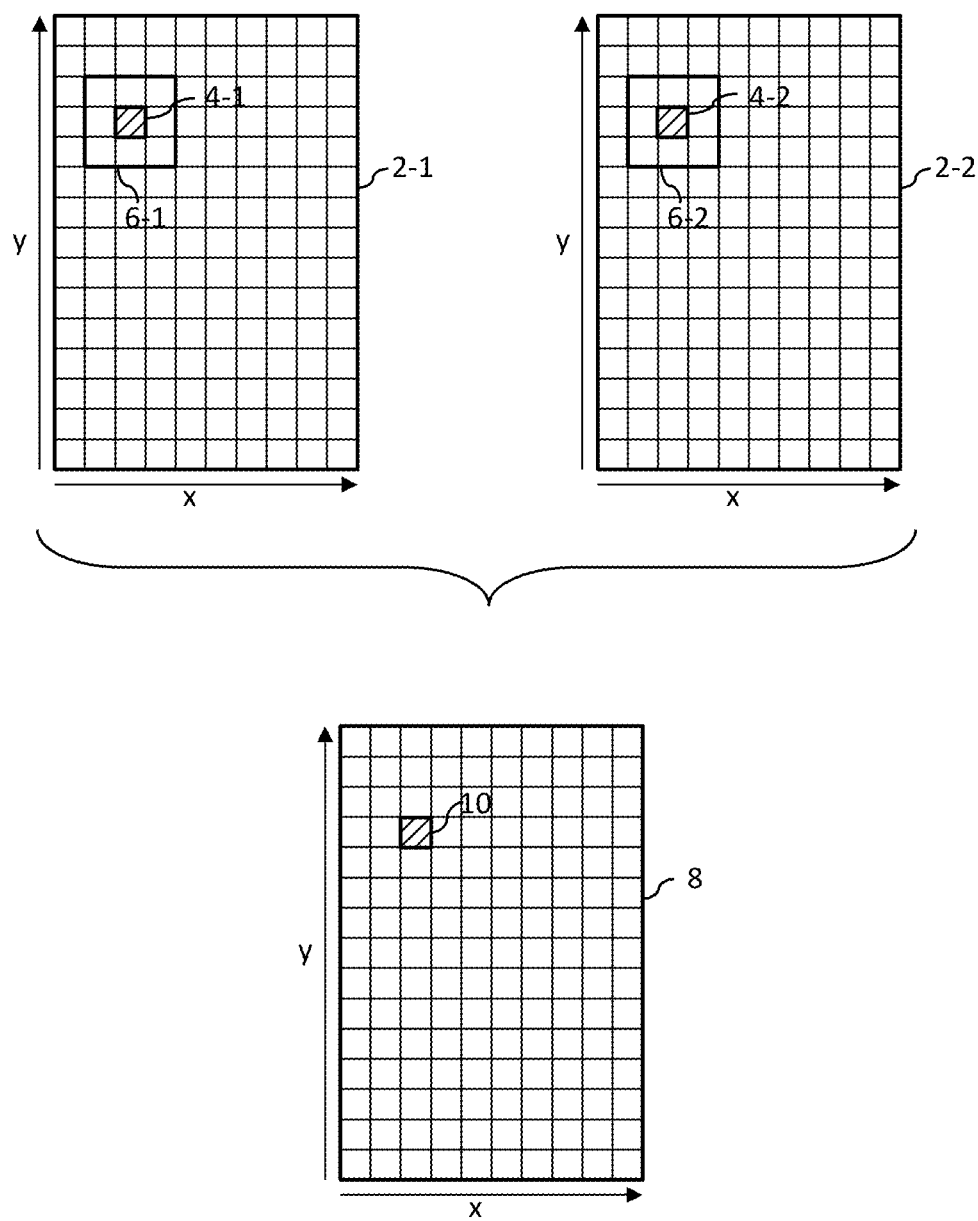
FIG. 7 is a schematic illustrating an aspect of how the accumulator array is processed in process S200 in FIG. 4.
Figure 8:
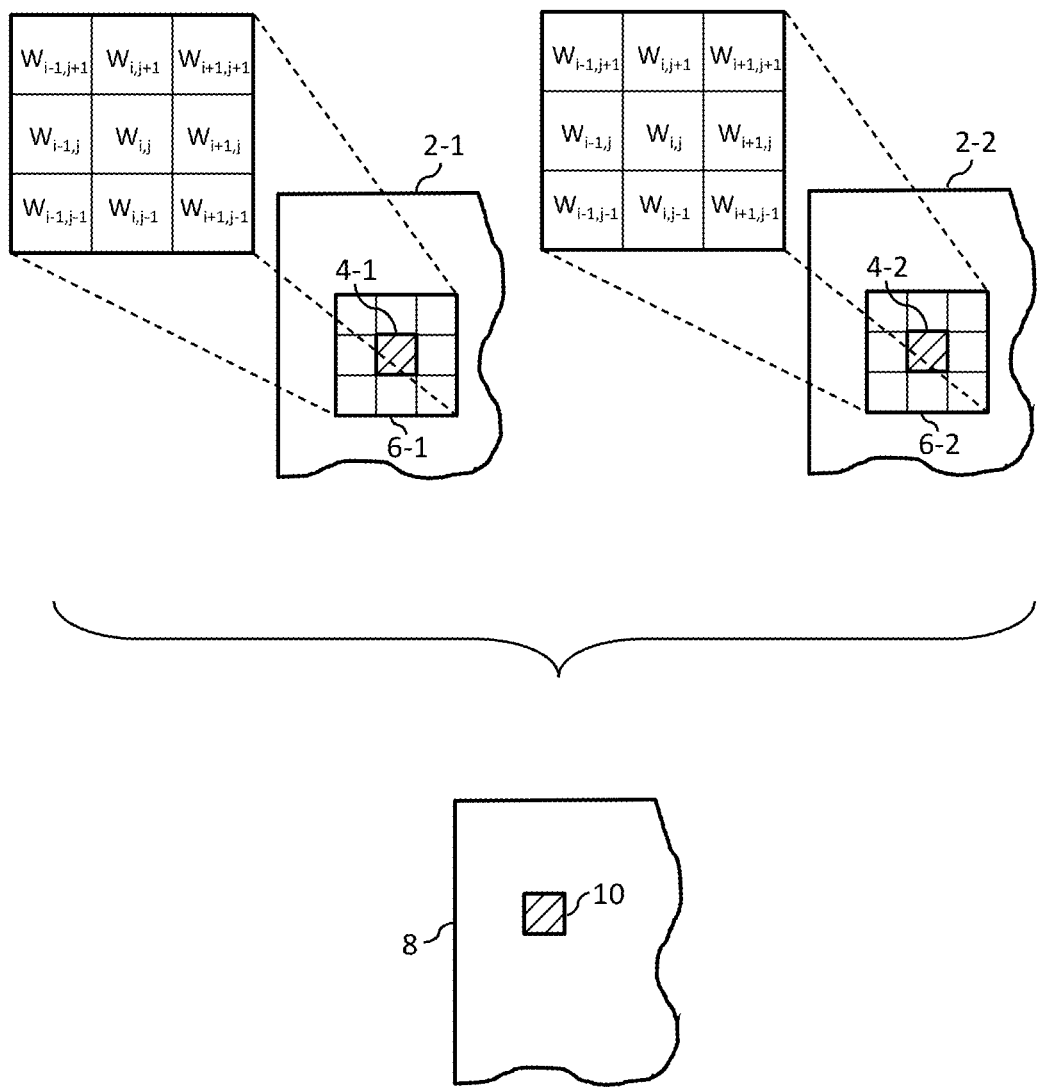
FIG. 8 is a schematic illustrating an aspect of how the accumulator array is processed in a variant of process S200 in FIG. 4.

Referring firstly to FIG. 4, in process S100, the image processing apparatus 140 receives from the tracking image acquisition module 120 a first image based on one or more of the received images and a second image based on another one or more of the received images, and registers the first and second images with respect to each other. It is noted that the first image may be acquired and/or stored before or after the second image. By way of an example, the first image may be obtained by averaging two or more of the received images, and the second image may be obtained by averaging two or more other received images. In the present embodiment, however, the image processing apparatus receives from the tracking image acquisition module 120 a first and a second of the received images (which may, as in the present embodiment, be adjacent to each other in the sequence of acquired images) and registers the first and second images with respect to each other. The image processing apparatus 140 may calculate a cross-correlation between the first and second images and, based on the calculated cross-correlation, co-register the two images. The image processing apparatus 140 thus generates a registered second image 2-2 that is co-registered with the first image 2-1, as illustrated in FIG. 7. It should be noted, however, that the received images may alternatively be registered with each other by registering each of these images with respect to the reference image, so that the first and second images are registered with respect to the reference image and therefore with respect to one another.

It should also be noted that, although the retinal images processed by the image processing apparatus 140 are obtained directly from the tracking image acquisition module 120 in the present embodiment, the image processing apparatus 140 may alternatively perform the image processing operations described herein on images from the tracking image acquisition module 120 that have been pre-processed, for example to accentuate image features that are helpful for establishing co-alignment with the reference image in the manner described in U.S. Pat. No. 9,454,817, the contents of which are incorporated herein by reference in their entirely. In the described pre-processing method, image information can be considered to exist at a range of spatial frequencies and being accordingly partitioned into four classifications, namely: (i) large-scale information; (ii) medium-scale information relating to coarse (mainly choroidal) features; (iii) medium-scale information relating to fine (mainly vascular) features; and (iv) small-scale (textural) information. The information used in the present algorithm is mainly from the medium scale information consisting of vasculature and choroidal layers. The extraction of this information involves comparing (through 2D convolution) an image frame with a 'matched' kernel. In simple terms, this matched kernel can be thought of as having a 'shape' which is equivalent to the 'shape' being extracted. In order to extend the range of information being extracted, the kernel shape can be adjusted in a range between 'fine' and 'coarse'. These kernels can also be rotated and convolutions repeated at each alternative step in rotation, taking the maximum value for each convolution as the value that is assigned in the pre-processed image frame. Further details of the pre-processing algorithm are provided in U.S. Pat. No. 9,454,817, the contents of which are incorporated herein by reference in their entirely.

Although the image processing apparatus 140 may proceed to co-register each pair of retinal images without discrimination (i.e. non-selectively), the image processing apparatus 140 preferably only proceeds to co-register the images when the calculated cross-correlation between the two images satisfies a prescribed condition. This prescribed condition may, for example, be that a peak value of the cross-correlation exceeds a predetermined threshold. As another alternative, the prescribed condition may, as in the present embodiment, be that the value of a confidence F, which provides a measure of the likelihood of the translational and rotational offset values being correct, exceeds a predetermined threshold, $F_{Th}$. In this case, the threshold $F_{Th}$ may be set so that the number of true-negative occurrences (i.e. cases where values are reported with high confidence but are actually incorrect) is close to zero. The process by which the image processing apparatus 140 of the present embodiment registers the first and second images in process S100 will now be described in more detail with reference to FIG. 5.

Figure 6:
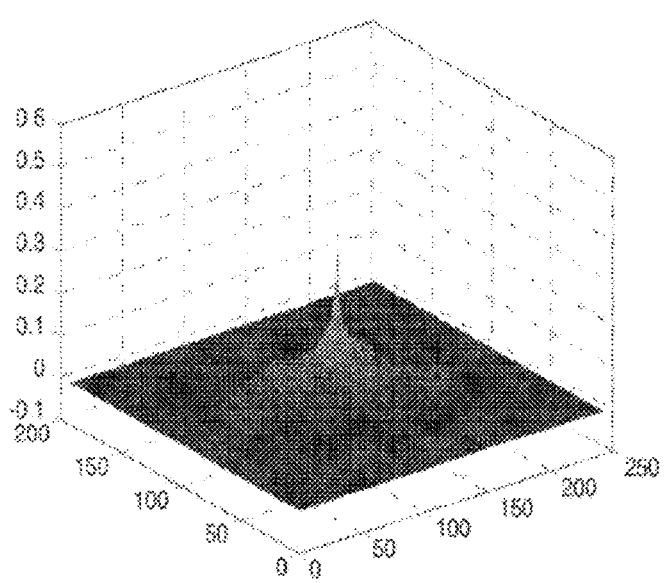
FIG. 6 is a schematic illustration of a correlation surface representing the result of cross-correlating a pair of images.

In process S110, the image processing apparatus 140 calculates a cross-correlation between a pair of adjacent images in the sequence of images. The values of the calculated cross-correlation define a correlation surface having a peak, as illustrated in FIG. 6.

In process S120, the image processing apparatus 140 calculates a confidence value, F, based on the calculated cross-correlation. The confidence value F may be obtained by parameterisation of the correlation surface, for example as described in U.S. Pat. No. 9,454,817, the contents of which are incorporated herein by reference in their entirety.

In process S130, the image processing apparatus 140 determines whether the calculated confidence value F exceeds the threshold value $F_{Th}$. In case the magnitude of the calculated confidence value F is determined in process S130 not to exceed the threshold value $F_{Th}$, the image processing apparatus 140 repeats processes S110 and S120 for first and second images in the next adjacent pair of images in the sequence (or, more generally, first and second images that based on respective one or more different received images). The loop comprising processes S110 to S130 is thus repeated until the calculated confidence value F exceeds the threshold value $F_{Th}$.

In process S140, the image processing apparatus 140 registers a first of the images with a second of the images, whose calculated cross-correlation value yields a confidence value F that exceeds the threshold value $F_{Th}$, to generate the registered second image 2-2 that is registered with the first image 2-1, as illustrated in FIG. 7.

It should be noted that the process of image registration described above with reference to FIG. 5 could additionally or alternatively be used by the image processing apparatus 140 to selectively output acquired offsets to the controller 130 for control of the OCT imaging module 110 to stabilise the scan location on the retina during the acquisition of the OCT images, so that only offsets associated with confidence values of $F > F_{Th}$ can be used for stabilising the scan location.

Referring again to FIG. 4, in process S200, the image processing apparatus 140 processes an array of pixels, referred to here as an "accumulator array of pixels", whose pixels values may all initially be set to zero, for example. As illustrated in FIG. 7, each pixel (e.g. the $(i, j)^{th}$ illustrated at "10") in the accumulator array 8 is associated with a correspondingly located pixel (in this example, the $(i, j)^{th}$ pixel labelled 4-1) in the first image 2-1 and a correspondingly located pixel (in this example, the $(i, j)^{th}$ pixel labelled 4-2) in the registered second image 2-2.

More particularly, the image processing apparatus 140 processes the accumulator array 8 by determining, for each pixel in the first image 2-1 and a correspondingly located pixel in the registered second image 2-2, whether the measure of similarity between a region of pixels (e.g. 6-1 in the case of pixel 4-1) surrounding the pixel in the first image 2-1 and an identically shaped region of pixels (e.g. 6-2 in the case of pixel 4-2) surrounding the corresponding pixel in the registered second image 2-2 exceeds a predefined level of similarity and, only when the measure of similarity exceeds the predefined level of similarity, changing (in this example, incrementing) a value of the pixel 10 in the accumulator array 8 associated with said pixel 4-1 in the first image 2-1 and with said correspondingly located pixel 4-2 in the registered second image 2-2. Although the pixel regions 6-1 and 6-2 in the present embodiment are 3×3 arrays of pixels in the present embodiment, the shape and size of the pixels regions is not so limited, and differently sized arrays (e.g. 9×9 pixels), which need not be square in shape, may alternatively be employed.

The image processing apparatus 140 may determine the degree of similarity between the corresponding pixel regions (e.g. as shown at 6-1 and 6-2 in FIG. 7), in one of a number of different ways. For example, the image processing apparatus 140 may, as in the present embodiment, use values of the pixels in the pixel regions 6-1 and 6-2 to determine the similarity between pixel value gradients (the pixel value gradient specifying a rate of change of pixel value with pixel location) in the x-direction and in the y-direction at correspondingly-located pixels 4-1 and 4-2 in the first and second co-registered images 2-1 and 2-2, and, only when (i) the gradients in the x-direction are the same for the two regions to within a first predefined margin, and (ii) the gradients in the y-direction are the same for the two regions to within a second predefined margin (which may or may not be the same as the first predefined margin), increment the value of the pixel 10 in the accumulator array 8 associated with pixel 4-1 in the first image 2-1 and with correspondingly located pixel 4-2 in the registered second image 2-2. The measure of similarity may additionally or alternatively be based on at least one of (i) a similarity between average pixel values, and (ii) a similarity between pixel value histograms, of the correspondingly located regions of pixels 6-1, 6-2 in the co-registered pairs of images 2-1, 2-2 in the sequence.

In the case of the pixel value histogram, the image processing apparatus 140 may generate a pixel value histogram of pixels values in each of pixel regions 6-1 and 6-2 (for example, by dividing the range of possible values that a pixel can take into a predetermined number of bins (e.g. 20 bins), and determining a respective cumulative count for each of these bins in accordance with the values of the pixels in the region), and, only when the similarity between the histograms is greater than a predefined level of similarity, increment the value of the pixel 10 in the accumulator array 8 associated with pixel 4-1 in the first image 2-1 and with correspondingly located pixel 4-2 in the registered second image 2-2. The similarity between the histograms may, for example, be determined by any suitable distance function, such as the Hellinger distance, Manhattan distance, Euclidian distance, Chebyshev distance, etc. This histogram-based similarity test may provide the most effective accentuation of retinal features in the reference image, although the other similarity tests described above may have the advantage of being less demanding of processing resources to implement and may therefore be preferably in cases where computational loading is a concern.

In a variant of process S200, the image processing apparatus 140 may also determine, for each pixel (e.g. 4-1) in the first image 2-1 and the correspondingly located pixel (e.g. 4-2) in the registered second image 2-2, whether a difference between a weighted average of pixel values in a region of pixels 6-1 surrounding the pixel 4-1 in the first image 2-1 and a weighted average of pixel values in a region of pixels 6-2 surrounding the correspondingly located pixel 4-2 in the registered second image 2-2 is less that a predefined threshold. In this variant of the process S200, the image processing apparatus 140 changes (e.g. increments) the value of the pixel 10 in the accumulator array 8 associated with the pixel 4-1 in the first image 2-1 and with the corresponding pixel 4-2 in the registered second image 2-2 only when the measure of similarity exceeds the predefined level of similarity and the difference between the weighted averages is less than the predefined threshold. In this variant, the weighted average of pixel values in the region of pixels 6-1 surrounding the pixel 4-1 in the first image 2-1, and the weighted average of pixel values in the region of pixels 6-2 surrounding the correspondingly located pixel 4-2 in the registered second image 2-2, are both calculated using a structuring element (as shown at "12" in FIG. 8) comprising pixel value weightings w to be applied to respective pixels in an arrangement of pixels as provided in pixel regions 6-1 and 6-2, wherein the structuring element 12 is set in a common one of a plurality of different orientations relative to the region of pixels 6-1 surrounding the pixel 4-1 in the first image 2-1 and the region of pixels 6-2 surrounding the correspondingly located pixel 4-2 in the registered second image 2-2 such that the weighted average of pixel values in the region of pixels 6-1 surrounding the pixel 4-1 in the first image 2-1 calculated for the common orientation is higher than the weighted averages of pixel values in the region of pixels 6-1 surrounding the pixel 4-1 in the first image 2-1 calculated for the other orientations. In other words, the orientation of the structuring element is varied among a plurality of different orientations (e.g. 10 different orientations) relative to the region of pixels 6-1 surrounding the pixel 4-1 in the first image 2-1 in order to identify the orientation that yields the greatest weighed average of pixel values in the first region of pixels 6-1, and that same orientation of the structuring element is then used to determine the weighted average of pixel values in the region of pixels 6-2 surrounding the correspondingly located pixel 4-2 in the registered second image 2-2. The additional 'structural' similarity test used in this variant of process S200 may be used to effectively reinforce pixel locations in the accumulator array 8 that are part of a characteristic shape (typically the vasculature or choroid features, or pathology structure which may depend on the wavelength of the illuminating light source) of the retinal features, with static features that are not part of the retina (e.g. edges of the eyelid or an eyelash, for example) being attenuated.

The reference image processed in process S20 in FIG. 3 may be defined by the accumulator array of pixels. Alternatively, the reference image may be obtained by processing the accumulator array. For example, the reference image may, as in the present embodiment, be obtained by generating a binarised version of the accumulator array. Accordingly, in (optional) process S300, the image processing apparatus 140 generates a binary reference image by setting the value of each pixel of the binary reference image to a first pixel value (e.g. "1") when a correspondingly located pixel 10 in the accumulator array 8 has a pixel value that exceeds a binarising threshold, and setting the value of each pixel of the binary reference image to a second value (e.g. "0") that is different from the first value when a correspondingly located pixel in the accumulator array has a pixel value that does not exceed the binarising threshold. The binary reference image may speed up the calculation of the cross-correlation with the received image in process S20.

In an alternative embodiment, the image processing apparatus 140 may generate a reference (grey scale) image by setting the value of each pixel of the reference image to the value of a correspondingly located pixel in the accumulator array 8 when the correspondingly located pixel in the accumulator array 8 has a pixel value that exceeds a second threshold, and setting the value of each pixel of the reference image to a first value (e.g. zero) when a correspondingly located pixel in the accumulator array 8 has a pixel value that does not exceed the second threshold. In this case, the accumulator array 8 may be processed such that the value of each pixel 10 therein is an accumulation (e.g. sum) of the values of correspondingly located pixels in all of the processed arrays of pixels, and the second threshold is typically smaller than, and increases with, the number of processed arrays of pixels.

In process S400, the image processing apparatus 140 determines whether there are at least two more images in the sequence to process. If there are, then processes S100 to S400 are repeated, as illustrated in FIG. 4, otherwise the process terminates.

As the values of some of the pixels in the accumulator array 8 increase with the repeated performance of process S200, the binarising threshold increases with the number of repetitions of process S200 in the present embodiment. For example, the binarising threshold may be half (or another predetermined fraction) of the number of repetitions of process S200.

Figure 9:
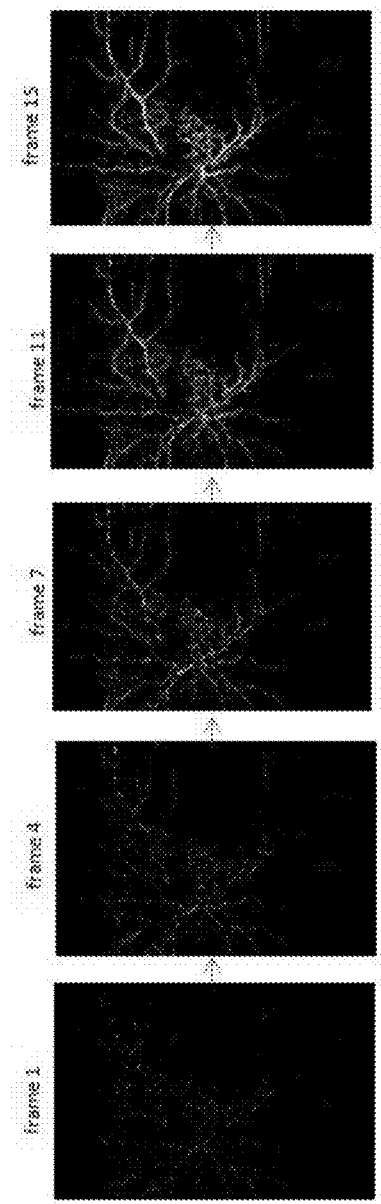
FIG. 9 shows images representative of the accumulator array described herein that illustrate how the accumulator array varies as the number of image frames processed by the image processing apparatus of the embodiment increases from 1 to 15.

FIG. 9 shows a sequence of images that are each representative of the content of the accumulator array, and illustrates how the accumulator array varies as the number of image frames processed by the image processing apparatus of the embodiment increases from 1 to 15. During the processing the accumulator array, the accumulation and enhancement of features (mainly vasculature in this example, but could be other features) can be readily seen.

Figure 10:
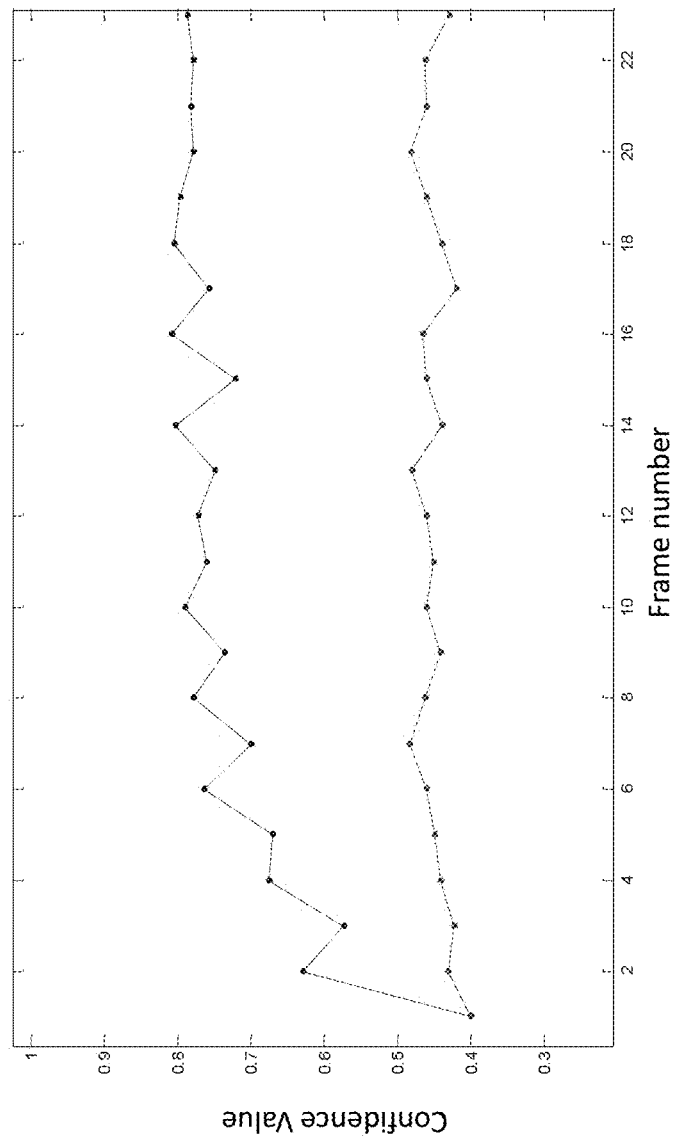
FIG. 10 illustrates the improvement in latch strength when tracking relative to the reference image in accordance with the embodiment, as compared to a fixed (unchanging) reference frame.

FIG. 10 illustrates the improvement in latch strength when tracking relative to the reference image in accordance with the embodiment, as compared to a fixed (unchanging) reference frame. In FIG. 10, the variation of the confidence values achieved when tracking relative to the evolving reference image frame over the first 31 frames of tracking is illustrated by the upper set of points, while the variation of the confidence values achieved when tracking relative to the fixed reference image frame is illustrated by the lower set of points. A clear improvement in confidence in the case of the evolving reference image as compared to the unchanging reference image can be observed.

In the above-described embodiment, the result of each comparison of pixel regions surrounding correspondingly located pixels in the co-registered images in process S200 is not stored after it has been determined to change or leave unchanged the correspondingly located pixel in the accumulator array, which has the advantage of requiring a relatively small amount of data to be stored while the sequence of retinal images is being processed. However, in another embodiment, the results of these comparisons of the co-registered images may be stored in a respective array of pixels, and all or only a predetermined number of most recent ones of these arrays of pixels may be stored in the image processing apparatus 140. Such an alternative second embodiment will now be described in more detail with reference to FIG. 11.

Figure 11:
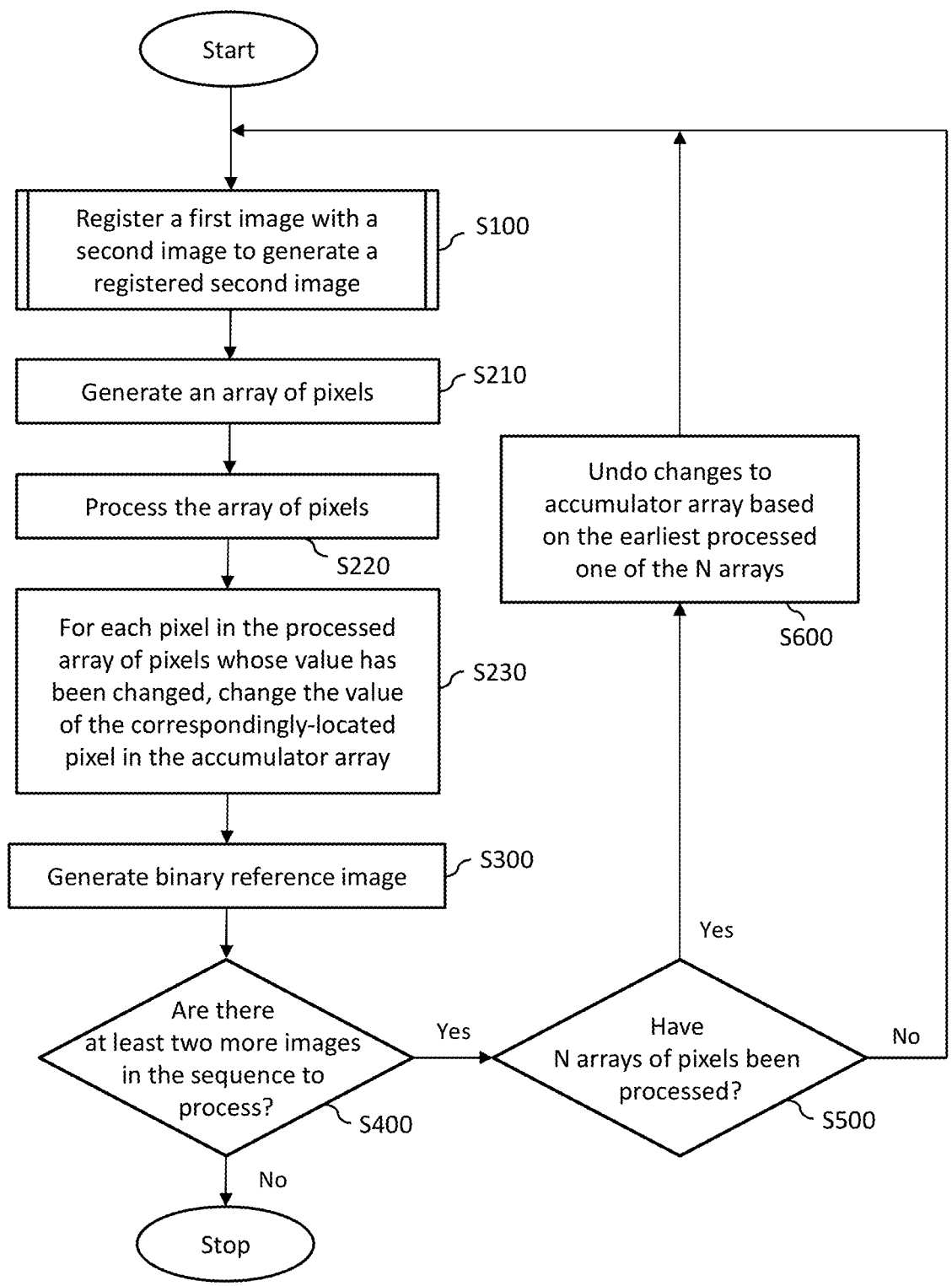
FIG. 11 is a flow diagram illustrating a process by which the reference image used in the process of FIG. 3 is modified to accentuate features therein representing structures of the imaged retina in relation to other features in the reference image in a second embodiment of the present invention.

Process S100 in FIG. 11 is the same as process S100 in FIG. 4 of the first embodiment, and its description will therefore not be repeated here.

In process S210, the image processing apparatus 140 generates an array of pixels, each pixel in the array being associated with a correspondingly located pixel (e.g. pixel 4-1 in FIG. 7) in the first image 2-1 and a correspondingly located pixel (4-2) in the registered second image 2-2.

In process S220, the image processing apparatus 140 processes the array of pixels by determining, for each pixel in the first image 2-1 and a correspondingly located pixel in the registered second image 2-2, whether the measure of similarity between the region of pixels (e.g. region 6-1 in FIG. 7) surrounding the pixel 4-1 in the first image 2-1 and the (identically shaped) region of pixels 6-2 surrounding the correspondingly located pixel 4-2 in the registered second image 2-2 exceeds the predefined level of similarity. The measure of similarity determined in this process is similar to that in process S200 in FIG. 4, and will therefore not be described again in detail. The image processing apparatus 140 changes (e.g. increments, as in the present example) a value of the pixel in the array associated with the pixel 4-1 in the first image 2-1 and with the correspondingly located pixel 4-2 in the registered second image 2-2 only when the measure of similarity exceeds the predefined level of similarity.

Similar to the variant of process S200 described above, the image processing apparatus 140 of the present embodiment may determine in process S220, for each pixel (e.g. 4-1) in the first image 2-1 and a correspondingly located pixel (4-2) in the registered second image 2-2, whether a difference between a weighted average of pixel values in a region of pixels 6-1 surrounding the pixel 4-1 in the first image 2-1 and a weighted average of pixel values in a region of pixels 6-2 surrounding the correspondingly located pixel 4-2 in the registered second image 2-2 is less that a predefined threshold and, only when the measure of similarity exceeds the predefined level of similarity and the difference is less than the predefined threshold, changing (e.g. incrementing) the value of the pixel in the array associated with said pixel 4-1 in the first image 2-1 and with said correspondingly located pixel 4-2 in the registered second image 2-2. The weighted average of pixel values in the region of pixels 6-1 surrounding the pixel 4-1 in the first image 2-1, and the weighted average of pixel values in the region of pixels 6-2 surrounding the correspondingly located pixel 4-2 in the registered second image 2-2, are both calculated using a structuring element 12 as described above with reference to FIG. 8.

In process S230, for each pixel in the processed array of pixels whose value has been incremented, the image processing apparatus 140 changes the value of the correspondingly located pixel 10 in the accumulator array 8. The image processing apparatus 140 may, as in the present embodiment, increment the value of the correspondingly located pixel 10 in the accumulator array 8 by the same amount (e.g. by 1) as the increment to the processed array, or alternatively by a different amount.

In process S300, the image processing apparatus 140 generates a binary reference image as in process S300 of the embodiment, and similarly determines (in process S400) whether there are at least two more images in the sequence of images to process. If not, then the processing terminates, as illustrated in FIG. 11. On the other hand, if the image processing apparatus 140 determines in process S400 that there are at least two more images in the sequence of images to process, the processing proceeds to process S500, wherein the image processing apparatus determines whether a predetermined number N (e.g. 10) of arrays of pixels have been generated and processed as described above. If fewer than N such arrays have been generated and processed, the processing loops back to process S100, as illustrated in FIG. 11. On the other hand, if the image processing apparatus determines in process S500 that N arrays of pixels have been generated and processed, then the image processing apparatus 140 undoes changes to the accumulator array 8 that were performed on the basis of the earliest processed one of the N stored arrays in process S600 (and optionally deletes the earliest processed one of the N stored arrays in process S600), and the processing then loops back to process S100. The image processing device 140 thus stores only the N most recently processed arrays of pixels, with the accumulator array 8 representing the combined results of only those N most recently processed arrays.

In a modification of process S300 in the second embodiment, the image processing apparatus 140 may generate a reference (grey scale) image by setting the value of each pixel of the reference image to the value of a correspondingly located pixel in the accumulator array 8 when the correspondingly located pixel in the accumulator array 8 has a pixel value that exceeds a second threshold, and setting the value of each pixel of the reference image to a first value (e.g. zero) when a correspondingly located pixel in the accumulator array 8 has a pixel value that does not exceed the second threshold.

In the above-described second embodiment, the accumulator array is thus processed such that the value of each pixel therein is an accumulation (e.g. sum) of the values of correspondingly located pixels in the N most recently processed arrays of pixels, with the binarising threshold used in process S300 (or the second threshold used in the above-described modification of process S300) being a fixed number.

In a modification of the above-described second embodiment, processes S500 and S600 may be omitted and processing may loop back from process S400 directly to process S100 when there are at least two more images in the sequence to be processed, and the accumulator array 8 may be processed such that the value of each pixel therein is an accumulation (e.g. sum) of the values of correspondingly located pixels in all of the processed arrays of pixels. In this modification, the binarising threshold (or the second threshold used in the above-described modification of process S300) would typically be smaller than, and increase with, the number of processed arrays of pixels. For example, the binarising threshold (or second threshold) may be 50% (or another predetermined fraction) of the number of processed arrays of pixels. This threshold may, however, increase with the number of processed arrays of pixels only until a predetermined number of arrays of pixels have been processed, and then stay fixed as the accumulator array is subsequently processed such that the value of each pixel therein is an accumulation (e.g. sum) of the values of correspondingly located pixels in a predetermined number of the most recently processed arrays of pixels, as described above.

[Modifications and Variations]

Many modifications and variations can be made to the embodiments described above.

In the above-described embodiments, the reference image is defined by or based on an accumulator array of pixels. However, the image processing apparatus 140 need not make use of such pixel value array in order to modify the reference image. In a variant of the embodiments, the image processing apparatus may generate and modify a binary reference image for acquiring the offsets, based on a stored set of pixel value arrays, wherein each array contains the results of the operations performed in process S220 described above. More particularly, in a variant, the binary reference image is generated and modified by processes of:

(a) registering a first image 2-1 based on one or more of the received images with a second images based on another one or more of the received images to generate a registered second image 2-2 that is registered with the first image 2-1;

(b) generating an array of pixels, each pixel in the array being associated with a correspondingly located pixel 4-1 in the first image 2-1 and a correspondingly located pixel 4-2 in the registered second image 2-2;

(c) processing the array of pixels by determining, for each pixel 4-1 in the first image 2-1 and a correspondingly located pixel 4-2 in the registered second image 2-2, whether the measure of similarity between the region of pixels 6-1 surrounding the pixel 4-1 in the first image 2-1 and the region of pixels 6-2 surrounding the corresponding pixel 4-2 in the registered second image 2-2 exceeds the predefined level of similarity and, only when the measure of similarity exceeds the predefined level of similarity, changing (e.g. incrementing) a value of the pixel in the array associated with said pixel 4-1 in the first image 2-1 and with said correspondingly located pixel 4-2 in the registered second image 2-2 (the measures of similarity may be determined as described in the above-described embodiments and variants thereof);

repeating processes (a) to (c) for different ones of the first and second images to generate a plurality of arrays of pixels;

generating the binary reference image by setting each pixel of the binary reference image to a first pixel value (e.g. "1") when correspondingly located pixels in the plurality of arrays of pixels have pixel values whose accumulated value (e.g. sum) exceeds a binarising threshold, and by setting the value of each pixel of the binary reference image to a second pixel value (e.g. "0") different from the first pixel value when correspondingly located pixels in the plurality of arrays of pixels have pixel values whose accumulated value does not exceed the binarising threshold; and modifying the binary reference image by repeating processes (a) to (c) at least once, and setting each pixel of the binary reference image to the first pixel value when correspondingly located pixels in the plurality of arrays of pixels have pixel values whose accumulated value (e.g. sum) exceeds a second binarising threshold, and by setting the value of each pixel of the binary reference image to the second pixel value when correspondingly located pixels in the plurality of arrays of pixels have pixel values whose accumulated value does not exceed the second binarising threshold.

In the variant, the binary reference image may be modified by setting each pixel of the binary reference image to the first pixel value when correspondingly located pixels in a predetermined number of most recently processed ones of the processed arrays of pixels have pixel values whose accumulated value (e.g. sum) exceeds the second binarising threshold, and by setting the value of each pixel of the binary reference image to the second pixel value when correspondingly located pixels in the predetermined number of most recently processed ones of the processed arrays of pixels have pixel values whose accumulated value does not exceed the second binarising threshold, the second binarising threshold being a fixed number. Alternatively, the binary reference image may be modified by setting each pixel of the binary reference image to the first pixel value when correspondingly located pixels in all the processed arrays of pixels have pixel values whose accumulated value exceeds the second binarising threshold, and by setting the value of each pixel of the binary reference image to the second pixel value when correspondingly located pixels in all the processed arrays of pixels have pixel values whose accumulated value does not exceed the second binarising threshold, the second binarising threshold being smaller than, and increasing with, the number of processed arrays of pixels.

In another variant, instead of a binary reference image, a grey scale reference image is generated and modified by processes of:

(a) registering a first image 2-1 based on one or more of the received images with a second image based on another one or more of the received images to generate a registered second image 2-2 that is registered with the first image 2-1;

(b) generating an array of pixels, each pixel in the array being associated with a correspondingly located pixel 4-1 in the first image 2-1 and a correspondingly located pixel 4-2 in the registered second image 2-2; p1 (c) processing the array of pixels by determining, for each pixel 4-1 in the first image 2-1 and a correspondingly located pixel 4-2 in the registered second image 2-2, whether the measure of similarity between the region of pixels 6-1 surrounding the pixel 4-1 in the first image 2-1 and the region of pixels 6-2 surrounding the corresponding pixel 4-2 in the registered second image 2-2 exceeds the predefined level of similarity and, only when the measure of similarity exceeds the predefined level of similarity, changing a value of the pixel in the array associated with said pixel 4-1 in the first image 2-1 and with said correspondingly located pixel 4-2 in the registered second image 2-2;

(d) repeating processes (a) to (c) for different ones of the first and second images to generate a plurality of arrays of pixels;

(e) generating the reference image by setting each pixel of the reference image to an accumulation (e.g. sum) of the pixel values of correspondingly located pixels in the plurality of arrays of pixels when said accumulation exceeds a threshold, and by setting the value of each pixel of the reference image to a first pixel value when said accumulation does not exceed the threshold;

(f) modifying the reference image by repeating processes (a) to (c) at least once, and setting each pixel of the reference image to an accumulation (e.g. sum) of the pixel values of correspondingly located pixels in the plurality of arrays of pixels when said accumulation exceeds a second threshold, and by setting the value of each pixel of the reference image to the first pixel value when correspondingly located pixels in the plurality of arrays of pixels have pixel values whose accumulation (e.g. sum) does not exceed the second threshold.

In this variant, the grey scale reference image may be modified by setting each pixel of the reference image to an accumulation (e.g. sum) of the pixel values of correspondingly located pixels in the plurality of arrays of pixels when the correspondingly located pixels in a predetermined number of most recently processed ones of the processed arrays of pixels have pixel values whose accumulation (e.g. sum) exceeds the second threshold, and by setting the value of each pixel of the reference image to the first pixel value when correspondingly located pixels in the predetermined number of most recently processed ones of the processed arrays of pixels have pixel values whose accumulation (e.g. sum) does not exceed the second threshold, the second threshold being a fixed number. Alternatively, the grey scale reference image may be modified by setting each pixel of the reference image to an accumulation (e.g. sum) of the pixel values of correspondingly located pixels in the plurality of arrays of pixels when the correspondingly located pixels in all the processed arrays of pixels have pixel values whose accumulation (e.g. sum) exceeds the second threshold, and by setting the value of each pixel of the reference image to the first pixel value (such as zero) when correspondingly located pixels in all the processed arrays of pixels have pixel values whose accumulation (e.g. sum) does not exceed the second threshold, the second threshold being smaller than, and increasing with, the number of processed arrays of pixels.

The invention claimed is:

1. A method of processing a sequence of images of a retina acquired by an ophthalmic device to generate retinal position tracking information that is indicative of a movement of the retina during the acquisition of the sequence of images, the method comprising:
   (i) receiving one or more images of the retina;
   (ii) calculating a cross-correlation between a reference image and an image based on the one or more received images to acquire an offset between the image and the reference image; and
   repeating processes (i) and (ii) to acquire, as the retinal position tracking information, respective offsets for the images that are based on the respective one or more received images; and
   modifying the reference image while processes (i) and (ii) are being repeated, by determining a measure of similarity between correspondingly located regions of pixels in two or more of the received images and accentuating features in the reference image representing structures of the imaged retina in relation to other features in the reference image based on the determined measure of similarity.

2. The method according to claim 1, wherein the reference image is defined by or based on an accumulator array of pixels, and the reference image is modified by processing the accumulator array of pixels by:
   (a) registering a first image based on one or more of the received images with a second image based on another one or more of the received images to generate a registered second image that is registered with the first image, each pixel in the accumulator array being associated with a correspondingly located pixel in the first image and a correspondingly located pixel in the registered second image;
   (b) processing the accumulator array by determining, for each pixel in the first image and a correspondingly located pixel in the registered second image, whether the measure of similarity between a region of pixels surrounding the pixel in the first image and a region of pixels surrounding the corresponding pixel in the registered second image exceeds a predefined level of similarity and, only when the measure of similarity exceeds the predefined level of similarity, changing a value of the pixel in the accumulator array associated with said pixel in the first image and with said correspondingly located pixel in the registered second image; and
   repeating processes (a) and (b) for different ones of the first and second images.

3. The method of claim 2, wherein processing the accumulator array in process (b) further comprises:
   determining, for each pixel in the first image and a correspondingly located pixel in the registered second image, whether a difference between a weighted average of pixel values in a region of pixels surrounding the pixel in the first image and a weighted average of pixel values in a region of pixels surrounding the correspondingly located pixel in the registered second image is less than a predefined threshold and, only when the measure of similarity exceeds the predefined level of similarity and the difference is less than the predefined threshold, changing the value of the pixel in the accumulator array associated with said pixel in the first image and with said corresponding pixel in the registered second image,
   wherein the weighted average of pixel values in the region of pixels surrounding the pixel in the first image, and the weighted average of pixel values in the region of pixels surrounding the correspondingly located pixel in the registered second image, are both calculated using a structuring element comprising pixel value weightings, the structuring element being set in a common one of a plurality of different orientations relative to the region of pixels surrounding the pixel in the first image and the region of pixels surrounding the correspondingly located pixel in the registered second image such that the weighted average of pixel values in the region of pixels surrounding the pixel in the first image calculated for the common orientation is higher than the weighted averages of pixel values in the region of pixels surrounding the pixel in the first image calculated for the other orientations.

4. The method according to claim 2, wherein the accumulator array is processed by:
   (a) registering a first image based on one or more of the received images with a second image based on another one or more of the received images to generate a registered second image that is registered with the first image, each pixel in the accumulator array being associated with a correspondingly located pixel in the first image and a correspondingly located pixel in the registered second image;
   (b1) generating an array of pixels, each pixel in the array being associated with a correspondingly located pixel in the first image and a correspondingly located pixel in the registered second image;
   (b2) processing the array of pixels by determining, for each pixel in the first image and a correspondingly located pixel in the registered second image, whether the measure of similarity between the region of pixels surrounding the pixel in the first image and the region of pixels surrounding the correspondingly located pixel in the registered second image exceeds the predefined level of similarity and, only when the measure of similarity exceeds the predefined level of similarity, changing a value of the pixel in the array associated with said pixel in the first image and with said correspondingly located pixel in the registered second image;

(b3) for each pixel in the processed array of pixels whose value has been changed, changing the value of the correspondingly located pixel in the accumulator array; and repeating processes (a) and (b1) to (b3) for different ones of the first and second images.

5. The method according to claim 4, wherein processing the array of pixels in process (b2) further comprises:

determining, for each pixel in the first image and a correspondingly located pixel in the registered second image, whether a difference between a weighted average of pixel values in a region of pixels surrounding the pixel in the first image and a weighted average of pixel values in a region of pixels surrounding the correspondingly located pixel in the registered second image is less than a predefined threshold and, only when the measure of similarity exceeds the predefined level of similarity and the difference is less than the predefined threshold, changing the value of the pixel in the array associated with said pixel in the first image and with said correspondingly located pixel in the registered second image, wherein the weighted average of pixel values in the region of pixels surrounding the pixel in the first image, and the weighted average of pixel values in the region of pixels surrounding the correspondingly located pixel in the registered second image, are both calculated using a structuring element comprising pixel value weightings, the structuring element being set in a common one of a plurality of different orientations relative to the region of pixels surrounding the pixel in the first image and the region of pixels surrounding the correspondingly located pixel in the registered second image such that the weighted average of pixel values in the region of pixels surrounding the pixel in the first image calculated for the common orientation is higher than the weighted averages of pixel values in the region of pixels surrounding the pixel in the first image calculated for the other orientations.

6. The method according to claim 2, wherein the reference image is generated by:

setting the value of each pixel of the reference image to the value of a correspondingly located pixel in the accumulator array when the correspondingly located pixel in the accumulator array has a pixel value that exceeds a second threshold; and setting the value of each pixel of the reference image to a first value when a correspondingly located pixel in the accumulator array has a pixel value that does not exceed the second threshold.

7. The method according to claim 2, wherein the reference image is a binary reference image generated by:

setting the value of each pixel of the binary reference image to a first pixel value when a correspondingly located pixel in the accumulator array has a pixel value that exceeds a second threshold; and setting the value of each pixel of the binary reference image to a second value when a correspondingly located pixel in the accumulator array has a pixel value that does not exceed the second threshold.

8. The method according to claim 6 or claim 7, wherein the accumulator array is processed by:

(a) registering a first image based on one or more of the received images with a second image based on another one or more of the received images to generate a registered second image that is registered with the first image, each pixel in the accumulator array being associated with a correspondingly located pixel in the first image and a correspondingly located pixel in the registered second image;

(b1) generating an array of pixels, each pixel in the array being associated with a correspondingly located pixel in the first image and a correspondingly located pixel in the registered second image;

(b2) processing the array of pixels by determining, for each pixel in the first image and a correspondingly located pixel in the registered second image, whether the measure of similarity between the region of pixels surrounding the pixel in the first image and the region of pixels surrounding the correspondingly located pixel in the registered second image exceeds the predefined level of similarity and, only when the measure of similarity exceeds the predefined level of similarity, changing a value of the pixel in the array associated with said pixel in the first image and with said correspondingly located pixel in the registered second image;

(b3) for each pixel in the processed array of pixels whose value has been changed, changing the value of the correspondingly located pixel in the accumulator array; and repeating processes (a) and (b1) to (b3) for different ones of the first and second images, and wherein the accumulator array is processed such that the value of each pixel therein is an accumulation of the values of correspondingly located pixels in a predetermined number of most recently processed ones of the processed arrays of pixels, and wherein the second threshold is a fixed number.

9. The method according to claim 6 or claim 7, wherein the accumulator array is processed by:

(a) registering a first image based on one or more of the received images with a second image based on another one or more of the received images to generate a registered second image that is registered with the first image, each pixel in the accumulator array being associated with a correspondingly located pixel in the first image and a correspondingly located pixel in the registered second image;

(b1) generating an array of pixels, each pixel in the array being associated with a correspondingly located pixel in the first image and a correspondingly located pixel in the registered second image;

(b2) processing the array of pixels by determining, for each pixel in the first image and a correspondingly located pixel in the registered second image, whether the measure of similarity between the region of pixels surrounding the pixel in the first image and the region of pixels surrounding the correspondingly located pixel in the registered second image exceeds the predefined level of similarity and, only when the measure of similarity exceeds the predefined level of similarity, changing a value of the pixel in the array associated with said pixel in the first image and with said correspondingly located pixel in the registered second image;

(b3) for each pixel in the processed array of pixels whose value has been changed, changing the value of the correspondingly located pixel in the accumulator array; and repeating processes (a) and (b1) to (b3) for different ones of the first and second images, and wherein the accumulator array is processed such that the value of each pixel therein is an accumulation of the values of correspondingly located pixels in all of the processed arrays of pixels, and the second threshold increases with the number of processed arrays of pixels.

10. The method according to claim 1, wherein the reference image is a binary reference image, and is generated and modified by:

(a) registering a first image based on one or more of the received images with a second image based on another one or more of the received images to generate a registered second image that is registered with the first image;

(b) generating an array of pixels, each pixel in the array being associated with a correspondingly located pixel in the first image and a correspondingly located pixel in the registered second image;

(c) processing the array of pixels by determining, for each pixel in the first image and a correspondingly located pixel in the registered second image, whether the measure of similarity between the region of pixels surrounding the pixel in the first image and the region of pixels surrounding the corresponding pixel in the registered second image exceeds the predefined level of similarity and, only when the measure of similarity exceeds the predefined level of similarity, changing a value of the pixel in the array associated with said pixel in the first image and with said correspondingly located pixel in the registered second image;

(d) repeating processes (a) to (c) for different ones of the first and second images to generate a plurality of arrays of pixels;

(e) generating the binary reference image by setting each pixel of the binary reference image to a first pixel value when correspondingly located pixels in the plurality of arrays of pixels have pixel values whose accumulation exceeds a binarising threshold, and by setting the value of each pixel of the binary reference image to a second pixel value when correspondingly located pixels in the plurality of arrays of pixels have pixel values whose accumulation does not exceed the binarising threshold;

(f) modifying the binary reference image by repeating processes (a) to (c) at least once, and setting each pixel of the binary reference image to the first pixel value when correspondingly located pixels in the plurality of arrays of pixels have pixel values whose accumulation exceeds a second binarising threshold, and by setting the value of each pixel of the binary reference image to the second pixel value when correspondingly located pixels in the plurality of arrays of pixels have pixel values whose accumulation does not exceed the second binarising threshold.

11. The method according to claim 10, wherein the binary reference image is modified by setting each pixel of the binary reference image to the first pixel value when:

correspondingly located pixels in a predetermined number of most recently processed ones of the processed arrays of pixels have pixel values whose accumulation exceeds the second binarising threshold, and by setting the value of each pixel of the binary reference image to the second pixel value when correspondingly located pixels in the predetermined number of most recently processed ones of the processed arrays of pixels have pixel values whose accumulation does not exceed the second binarising threshold, the second binarising threshold being a fixed number.

12. The method according to claim 10, wherein the binary reference image is modified by setting each pixel of the binary reference image to the first pixel value when correspondingly located pixels in all the processed arrays of pixels have pixel values whose accumulation exceeds the second binarising threshold, and by setting the value of each pixel of the binary reference image to the second pixel value when correspondingly located pixels in all the processed arrays of pixels have pixel values whose accumulation does not exceed the second binarising threshold, the second binarising threshold increasing with the number of processed arrays of pixels.

13. The method according to claim 1, wherein the reference image is generated and modified by:

(a) registering a first image based on one or more of the received images with a second image based on another one or more of the received images to generate a registered second image that is registered with the first image;

(b) generating an array of pixels, each pixel in the array being associated with a correspondingly located pixel in the first image and a correspondingly located pixel in the registered second image;

(c) processing the array of pixels by determining, for each pixel in the first image and a correspondingly located pixel in the registered second image, whether the measure of similarity between the region of pixels surrounding the pixel in the first image and the region of pixels surrounding the corresponding pixel in the registered second image exceeds the predefined level of similarity and, only when the measure of similarity exceeds the predefined level of similarity, changing a value of the pixel in the array associated with said pixel in the first image and with said correspondingly located pixel in the registered second image;

(d) repeating processes (a) to (c) for different ones of the first and second images to generate a plurality of arrays of pixels;

(e) generating the reference image by setting each pixel of the reference image to an accumulation of the pixel values of correspondingly located pixels in the plurality of arrays of pixels when said accumulation exceeds a threshold, and by setting the value of each pixel of the reference image to a first pixel value when said accumulation does not exceed the threshold;

(f) modifying the reference image by repeating processes (a) to (c) at least once, and setting each pixel of the reference image to an accumulation of the pixel values of correspondingly located pixels in the plurality of arrays of pixels when said accumulation exceeds a second threshold, and by setting the value of each pixel of the reference image to the first pixel value when correspondingly located pixels in the plurality of arrays of pixels have pixel values whose accumulation does not exceed the second threshold.

14. The method according to claim 13, wherein the reference image is modified by setting each pixel of the reference image to an accumulation of the pixel values of correspondingly located pixels in the plurality of arrays of pixels when:

the correspondingly located pixels in a predetermined number of most recently processed ones of the processed arrays of pixels have pixel values whose accumulation exceeds the second threshold, and by setting the value of each pixel of the reference image to the first pixel value when correspondingly located pixels in the predetermined number of most recently processed ones of the processed arrays of pixels have pixel values whose accumulation does not exceed the second threshold, the second threshold being a fixed number.

15. The method according to claim 13, wherein the reference image is modified by setting each pixel of the reference image to an accumulation of the pixel values of correspondingly located pixels in the plurality of arrays of pixels when the correspondingly located pixels in all the processed arrays of pixels have pixel values whose accumulation exceeds the second threshold, and by setting the value of each pixel of the reference image to the first pixel value when correspondingly located pixels in all the processed arrays of pixels have pixel values whose accumulation does not exceed the second threshold, the second threshold increasing with the number of processed arrays of pixels.

16. The method according to claim 2, wherein process (a) comprises:
    (a1) calculating a cross-correlation between a pair of images in the sequence of images, wherein values of the calculated cross-correlation define a correlation surface having a peak;
    (a2) calculating a confidence value based on the calculated 10 cross-correlation;
    (a3) determining whether the calculated confidence value exceeds a confidence threshold value;
    (a4) in case the magnitude of the calculated confidence value is determined not to exceed the confidence threshold value, repeating processes (a1) to (a3) for first and second images in one or more following images in the sequence, until the calculated confidence value exceeds the confidence threshold value; and
    registering a first of the images with a second of the images, whose calculated cross-correlation value yields a confidence value that exceeds the confidence threshold value, to generate the registered second image that is registered with the first image.

17. The method according to claim 1, wherein the offset is at least one of a translational offset and a rotational offset between the reference image and the image that is based on the received one or more images.

18. The method according to claim 1, wherein the measure of similarity is based on at least one of:
    (i) a similarity between a pixel value gradient;
    (ii) a similarity between an average pixel value; and
    (iii) a similarity between a pixel value histogram,
    of the correspondingly located regions of pixels in the two or more images in the sequence.

19. A non-transitory computer-readable storage medium storing computer program instructions which, when executed by a processor, cause the processor to process a sequence of images of a retina acquired by an ophthalmic device to generate retinal position tracking information that is indicative of a movement of the retina during the acquisition of the sequence of images, by:
    (i) receiving one or more images of the retina;
    (ii) calculating a cross-correlation between a reference image and an image based on the one or more received images to acquire an offset between the image and the reference image; and
    repeating processes (i) and (ii) to acquire, as the retinal position tracking information, respective offsets for the images that are based on the respective one or more received images; and
    modifying the reference image while processes (i) and (ii) are being repeated, by determining a measure of similarity between correspondingly located regions of pixels in two or more of the received images and accentuating features in the reference image representing structures of the imaged retina in relation to other features in the reference image based on the determined measure of similarity.

20. An image processing apparatus configured to process a sequence of images of a retina acquired by an ophthalmic device to generate retinal position tracking information indicative of a movement of the retina during the acquisition of the sequence of images, the image processing apparatus comprising a processor and a memory storing computer program instructions which, when executed by the processor cause the processor to
    process the sequence of images of the retina to generate the retinal position tracking information by:
    (i) receiving one or more images of the retina;
    (ii) calculating a cross-correlation between a reference image and an image based on the one or more received images to acquire an offset between the image and the reference image; and
    repeating processes (i) and (ii) to acquire, as the retinal position tracking information, respective offsets for the images that are based on the respective one or more received images; and
    modifying the reference image while processes (i) and (ii) are being repeated, by determining a measure of similarity between correspondingly located regions of pixels in two or more of the received images and accentuating features in the reference image representing structures of the imaged retina in relation to other features in the reference image based on the determined measure of similarity.

21. An ophthalmic device comprising:
    an optical coherence tomography, OCT, imaging module configured to acquire OCT images of a retina of an eye by scanning a beam of light across the retina and processing a reflection of the beam from the retina;
    a tracking image acquisition module configured to acquire a sequence of images of the retina for tracking a movement of the retina while the OCT imaging module acquires the OCT images; and
    a controller comprising an image processing apparatus that is configured to process the sequence of images to generate retinal position tracking information indicative of the movement of the retina during the acquisition of the OCT images, the controller being configured to control the OCT imaging module using the retinal position tracking information so as to stabilise the beam during the acquisition of the OCT images,
    wherein the image processing apparatus comprises a processor and a memory storing computer program instructions which, when executed by the processor, cause the processor to process the sequence of images of the retina to generate the retinal position tracking information by:
    (i) receiving one or more images of the retina;
    (ii) calculating a cross-correlation between a reference image and an image based on the one or more received images to acquire an offset between the image and the reference image; and repeating processes (i) and (ii) to acquire, as the retinal position tracking information, respective offsets for the images that are based on the respective one or more received images; and modifying the reference image while processes (i) and (ii) are being repeated, by determining a measure of similarity between correspondingly located regions of pixels in two or more of the received images and accentuating features in the reference image representing structures of the imaged retina in relation to other features in the reference image based on the determined measure of similarity.

\* \* \* \* \*